(12) United States Patent
Frodl et al.

(10) Patent No.: US 7,977,638 B2
(45) Date of Patent: Jul. 12, 2011

(54) LONG-TERM STABLE OPTICAL SENSOR ARRANGEMENT, ESPECIALLY A HYDROGEN SENSOR, AND COMBINED GAS SENSOR ARRANGEMENT

(75) Inventors: Robert Frodl, München (DE); Thomas Tille, München (DE)

(73) Assignee: Bayerische Motoren Werke Aktiengesellschaft, Munich (DE)

( * ) Notice: Subject to any disclaimer, the term of this patent is extended or adjusted under 35 U.S.C. 154(b) by 38 days.

(21) Appl. No.: 11/941,604

(22) Filed: Nov. 16, 2007

(65) Prior Publication Data
US 2008/0116378 A1 May 22, 2008

(30) Foreign Application Priority Data

Nov. 16, 2006 (DE) .................. 10 2006 054 165

(51) Int. Cl.
*G01N 21/61* (2006.01)
*G01N 25/46* (2006.01)

(52) U.S. Cl. ............. 250/338.5; 250/343; 250/344; 250/339.13; 356/432; 436/144; 73/1.06; 73/1.02; 385/12

(58) Field of Classification Search ............ 356/432, 356/437; 422/88, 82.06, 82.05, 82.09; 73/1.02, 73/1.06; 250/343, 338.5, 344, 564, 339.13; 385/12
See application file for complete search history.

(56) References Cited

U.S. PATENT DOCUMENTS

| | | | |
|---|---|---|---|
| 4,661,320 A | * | 4/1987 | Ito et al. ................. 422/86 |
| 4,755,667 A | * | 7/1988 | Marsoner et al. ......... 250/227.24 |
| 4,872,759 A | | 10/1989 | Stich-Baumeister et al. |
| 5,783,152 A | | 7/1998 | Nave |
| 6,006,582 A | * | 12/1999 | Bhandari et al. ............ 73/23.2 |

(Continued)

FOREIGN PATENT DOCUMENTS

JP 61201141 A 9/1986

(Continued)

OTHER PUBLICATIONS

Okuhara et al., "Influence of phase transformation in Pd hydride on the recovery characteristics of optical hydrogen sensors," Bulletin or Material Science, vol. 22, No. 6, Oct. 1999, pp. 999-1001, Indian Academy of Sciences.*

(Continued)

*Primary Examiner* — David P Porta
*Assistant Examiner* — Yara B Green
(74) *Attorney, Agent, or Firm* — Barley Snyder LLC (57) ABSTRACT

The present invention relates to optical sensor arrangements, especially sensors of the type that can be used in motor vehicles and which can detect hydrogen in a gaseous measured medium. According to the invention, an optical sensor arrangement has the at least one radiation source (108) for emitting radiation, the at least one measuring transducer which modifies its optical characteristics in response to the presence and/or concentration of at least one analyte in a measured medium (104) and is arranged so that it interacts with at least part of the emitted radiation (110), a first detector unit (112) for capturing a change in radiant intensity due to the changed optical characteristics of the measuring transducer and for outputting a first measuring signal and a light conducting body (106) which is transparent to the emitted radiation, wherein the measuring transducer, which is sensitive to the analyte, is arranged on at least one surface of the light conducting body (106) so that the emitted radiation impinges on a surface of the measuring transducer which faces away from the measured medium (104).

22 Claims, 6 Drawing Sheets

U.S. PATENT DOCUMENTS

| | | | |
|---|---|---|---|
| 6,704,470 B1 * | 3/2004 | Schneider et al. | 385/12 |
| 6,762,871 B2 * | 7/2004 | Yoshimura | 359/265 |
| 6,843,102 B1 * | 1/2005 | Shulga et al. | 73/25.01 |
| 2002/0148948 A1 * | 10/2002 | Hensel | 250/214.1 |
| 2004/0061919 A1 * | 4/2004 | Tench et al. | 359/265 |

FOREIGN PATENT DOCUMENTS

| | | |
|---|---|---|
| JP | 62170828 A | 7/1987 |
| JP | 2005-83832 | 3/2005 |
| JP | 2005265590 A | 9/2005 |
| WO | WO 00/75634 A1 * | 12/2000 |

OTHER PUBLICATIONS

Michael A. Butler "Micromirror Optical-Fiber Hydrogen Sensor" Sensor and Actuators B 22 (1994) pp. 155-163 (9pages).

K. Ito and T. Ohgami "Hydrogen Detection Based on Coloration of Anodic Tungsten Oxide Film" Feb. 24, 1992, p. 938-940.

* cited by examiner

LONG-TERM STABLE OPTICAL SENSOR ARRANGEMENT, ESPECIALLY A HYDROGEN SENSOR, AND COMBINED GAS SENSOR ARRANGEMENT

CROSS-REFERENCE TO RELATED APPLICATIONS

This application claims the benefit of the filing date under 35 U.S.C. §119(a)-(d) of patent application No. DE 10 2006 054 165.0, filed Nov. 16, 2006.

FIELD OF THE INVENTION

The present invention relates to an optical sensor arrangement for detecting at least one analyte in a measured medium, especially optical-based hydrogen sensors. The present invention also relates to a combined gas sensor arrangement for detecting hydrogen and at least one other gas.

BACKGROUND

Fossil fuels such as petroleum and natural gas which have so far been the most widely used fuels for motor vehicles and heating purposes are becoming scarce, are expensive and are not renewable. This is why alternative energy sources, which mainly use hydrogen as a transportable energy carrier in combination with a fuel cell, for example, are attracting more and more attention. It can therefore be assumed that hydrogen gas sensors will be needed on an increasingly large scale in both automotive and heating applications. Such hydrogen sensors can be used for determining concentration levels to allow optimized control of fuel cells as well as to fulfill alerting functions in situations where threshold levels must be detected. In order to ensure adequate safety, especially in monitoring applications, it is desirable that such hydrogen sensors are rugged and reliable and that they can be manufactured and miniaturized simply and inexpensively and be fitted, where possible, as an integrated unit.

The use of infrared gas sensors, which determine the presence and/or concentration of the gas in question by analyzing the absorption characteristics of the gas to be detected in a quite specific wavelength range in order to detect polar gases, such as methane or carbon dioxide, is known. Such gas sensors have a radiation source, an absorption path and a radiation detector. The radiant intensity measured by the radiation detector is a measure of the concentration of the absorbing gas; either a broadband radiation source can be used and the wavelength of interest can be adjusted via an interference filter or grate or a selective radiation source can be used, for instance a light-emitting diode or a laser in combination with light wavelength-selective radiation receivers. In the case of $CO_2$, the characteristic wavelength in the infrared wavelength range is at 4.24 µm.

The detection of carbon dioxide is becoming increasingly important in the automotive field. This is firstly due to the fact that the $CO_2$ content of the air in the interior of vehicles is monitored in order to increase the energy efficiency of heating and air conditioning systems so that, if necessary, i.e. if an increase in $CO_2$ concentration occurs, a supply of fresh air is introduced via an appropriate fan flap. Secondly, modern air-conditioning systems are based on $CO_2$ coolants and $CO_2$ gas sensors can therefore fulfill a monitoring function in conjunction with issuing $CO_2$ in the event of potential defects. In the automotive field in particular, sensors of this type must meet stringent requirements with respect to ruggedness, reliability and miniaturization and, at the same time, they must be extremely inexpensive to manufacture.

SUMMARY

An object of the present invention, among others is to provide a hydrogen sensor which is sufficiently rugged and reliable for use in the automotive field and also has a relatively long service life.

Another object of the present invention is to perform detection of more than one gas, especially to detect hydrogen and another gas such as carbon dioxide, in an especially simple and affordable manner.

The present invention is based primarily on the principle that the reliability of a hydrogen sensor can be improved, in the case of a hydrogen sensor which has a radiation source that emits radiation and a measuring transducer which modifies its optical characteristics in response to the presence and/or concentration of hydrogen, by attaching the measuring transducer to a light conducting body so that the emitted radiation impinges on a surface of the measuring transducer which faces away from the measured medium.

According to the invention, an optical sensor arrangement has the at least one radiation source for emitting radiation, the at least one measuring transducer which modifies its optical characteristics in response to the presence and/or concentration of at least one analyte in a measured medium and is arranged so that it interacts with at least part of the emitted radiation, a first detector unit for capturing a change in radiant intensity due to the changed optical characteristics of the measuring transducer and for outputting a first measuring signal and a light conducting body which is transparent to the emitted radiation, wherein the measuring transducer, which is sensitive to the analyte, is arranged on at least one surface of the light conducting body so that the emitted radiation impinges on a surface of the measuring transducer which faces away from the measured medium.

BRIEF DESCRIPTION OF THE DRAWINGS

The present invention is explained in greater detail below, reference being made to the exemplary embodiments shown in the accompanying drawings. Similar or corresponding details of the subject of the invention are denoted by identical reference numerals in the figures of which.

DETAILED DESCRIPTION OF THE EMBODIMENTS

Figure 1:
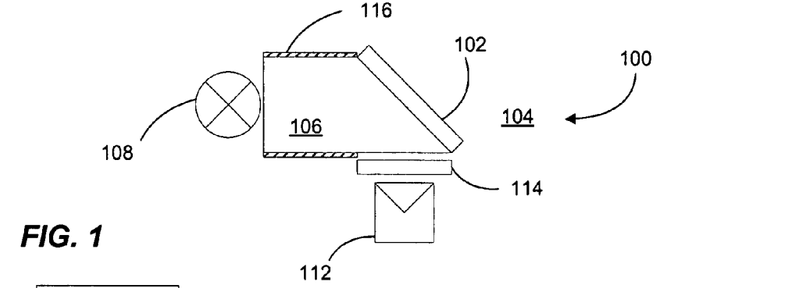
FIG. 1 is a schematic cross-section through a basic arrangement for an optical sensor arrangement in accordance with the present invention.

The construction and operating principle of the sensor arrangement according to the invention is explained in greater detail below using the example of an optical hydrogen sensor and making reference to the accompanying Figures. FIG. 1 shows a basic layout for the gas sensor arrangement in accordance with the invention in its simplest form. The description which follows assumes that the sensor is a hydrogen sensor. The principles according to the invention can, however, obviously also be used for other analytes for which sensitive layers which change their optical characteristics in case of inclusion of the analyte in question are available. Also, a test gas which contains the analyte(s) is referred to below as the measured medium 104. However, if the sensitive layer, often referred to below as the measuring transducer, and the other components are suitably designed, measurements can also be made in liquid media.

According to the invention, the sensor arrangement 100 has a gas-sensitive mirror as a measuring transducer 102. For example, this can be a hydrogen-sensitive mirror layer, the reflectivity of which varies in response to the presence and/or concentration of hydrogen as described in B. Farangis et al "A ROOM-TEMPERATURE OPERATED HYDROGEN SENSOR BASED ON NICKEL-MAGNESIUM FILMS", Poc. Of the 20th EUROSENSORS, Göteborg, Sweden, 17th-19th Sep. 2006, Paper T1C-P5.

According to the invention, the measuring transducer layer 102 is in contact with the test gas on a first surface. In order to be able to evaluate analysis of the transducer reaction with the measured medium 104, the measuring transducer layer 102 is in contact with a light conducting body 106 on a second surface which faces away from the measured medium 104. This light conducting body 106 is penetrated by radiation from a radiation source 108 in such a way that measuring the transducer layer 102 interacts with the emitted radiation 110.

In the embodiment shown, the transducer layer 102 slopes relative to the direction of emitted radiation 110 so that, at maximum reflectivity, approximately all the infrared radiation is reflected towards a detector unit 112. Optionally, a filter 114 can restrict the reflected radiation that impinges on the detector 112 to a specific wavelength range. If the concentration of the gas of interest in the measured medium 104 changes, the reflectivity of the transducer layer 102 changes and thus the intensity of the reflected radiation which can be measured on the detector unit also changes.

The side of the layer which is used for actual measurement does not come into contact with the measured medium 104, thus ensuring that the sensor arrangement offers improved measurement accuracy and a longer service life.

The radiation source 108 may emit an extremely wide range of wavelengths but, in the embodiment shown, it consists of an infrared radiation source, for instance a lamp, which emits a broadband light spectrum. Alternatively, light-emitting diodes (LEDs) could also be used.

Any suitable infrared detector can be used as the detector 112 and the method according to the invention can be adapted to suit the appropriate detector type.

For example, the detector 112 can be a pyro-element, an infrared thermopile or a photodiode. An appropriate suitable detector must be chosen depending on the particular requirements. A photodiode has the advantage of being a comparatively inexpensive component whereas a thermopile detector has the advantage of offering especially high, uniform absorption of radiation in the selected spectral range. Finally, pyroelectric sensors have the advantage of very high sensitivity and being easy to fabricate in miniaturized form which makes them highly suitable for integrated arrangements.

According to the invention, the light conducting body 106 may consist of a solid structure made of glass or plastic material, for example, which is transparent to the radiation of interest. This makes it possible, as shown clearly in relation to the arrangement in FIG. 11, to implement an integratable but modular structure wherein the measuring transducer can be replaced simply and quickly as needed. Under specific circumstances, for instance when detecting analyte molecules in a heavily contaminated environment, it is even conceivable to provide disposable light conducting bodies for one-off measurements.

In order to ensure as much radiation as possible on the transducer layer 102, the light conducting body 106 may have an optically opaque coating 116 on its other surfaces which are not needed for irradiation, interaction with the sensitive layer and radiating emissions onto the detector 112. The optically opaque coating is also intended to prevent extraneous light from entering the light conducting body, thereby distorting the signal.

Optical evaluation in the case of the basic arrangement in FIG. 1 is described in greater detail below, making reference to FIG. 2. The radiation source 108 is controlled by an electric control circuit 118 which can be designed as a separate unit or as part of a microcontroller. The lamp can be operated continuously or it can be pulsed at a specific frequency. A constant frequency and a specific pulse duty cycle are usually selected so as to avoid interference by using a narrow-band filter which has a filter frequency that matches the pulse frequency at which the radiation source is pulsed, for signal processing in the detector.

The emitted radiation 110 is reflected by the transducer layer 102 depending on the analyte content in the measured medium 104, the filter 114 allows the wavelength range of interest to pass through and it is detected by the detector 112. An evaluation unit (or evaluation circuit) 120 processes the output signal from the detector 112 and delivers an output signal that is correlated with the concentration of analyte in the measured medium 104 as an output 122 which is also referred to as the measuring signal.

Figure 2:
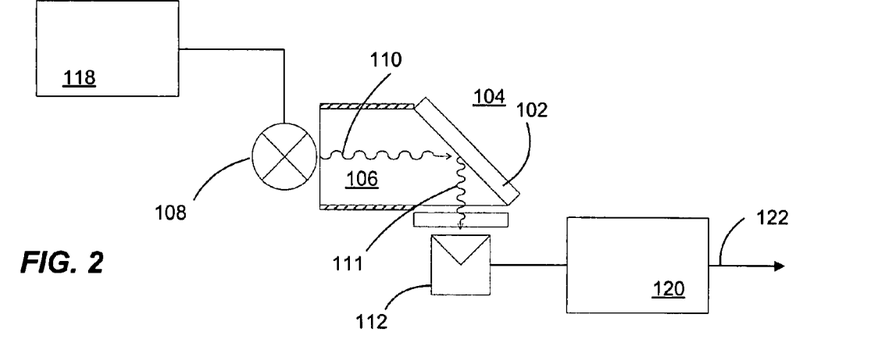
FIG. 2 is a schematic view of the optical evaluation circuit for the arrangement in FIG. 1.

However, in safety-relevant applications, for instance in the automotive field and in the case of applications which demand a long service life without any deterioration in reliability over time, using the arrangement shown in FIG. 2 poses the problem of ageing affects in any of the components, especially the radiation source 108, which can result in serious impairment of the sensor's characteristics. This is why, according to an advantageous embodiment of the present invention, the simple optical evaluation in FIG. 2 is enhanced by adding one or more redundant branches.

Figure 3:
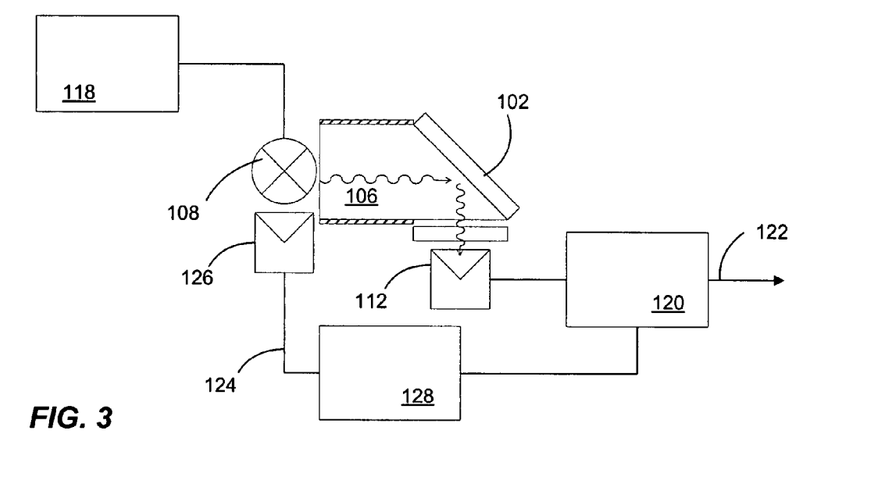
FIG. 3 is a schematic view of redundant analysis in accordance with the invention using another optical detector.

FIG. 3 shows a first possible way of producing such a redundant branch 124. In addition to the first detector 112 which analyses the reflected light beam 111 which is affected by the transducer layer 102, a second detector 126 is provided—this measures the radiation emitted by the radiation source 108 directly and makes it available as a reference value. Due to the second detector 126, lamp ageing can be compared independently of measurement effects and the effects of ageing of the transducer layer 102, thus providing an additional margin of safety. For example, it is possible to ascertain that the signal delivered by the actual measuring detector 112 is plausible because, for instance, the signal from the additional detector 126 must always be bigger than the signal from the first detector because there is no attenuation due to deflection by the light conducting body 106. This means that specific simple-optical-evaluation fault scenarios which occur during operation can be detected and possibly corrected in accordance with FIG. 2.

A correction unit 128 outputs, for instance, a correction factor to the evaluation circuit 120 which can be taken into account before the output signal 122 is delivered.

Figure 4:
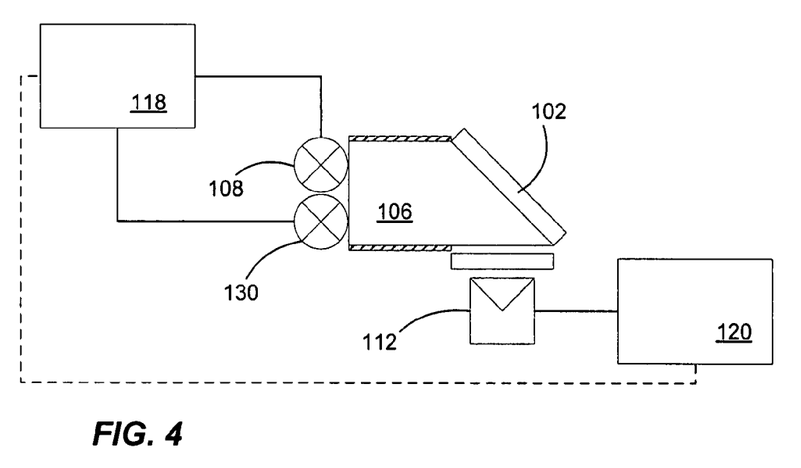
FIG. 4 shows the arrangement in FIG. 1 with an additional reference radiation source.

FIG. 4 shows a second possible way of implementing a redundant branch 124. In this embodiment, an additional reference radiation source 130 is provided in a similar manner to that which is known for $CO_2$ absorption sensors (see DE 199 25 196 A1). The reference radiation source 130 is only operated intermittently and it is assumed, by way of approximation, that the reference radiation source 130 essentially retains its original condition without ageing. The reference radiation source 130 is switched on at relatively long intervals in order to check the state of ageing of the actual measurement radiation source 108 and the evaluation circuit 120 determines the ageing of the measurement radiation source 108 from discrepancies between the output signals from the detector unit 112 when the reference radiation source 108 is switched on and when the measurement radiation source is switched on and compensates this ageing computationally if necessary.

Figure 5:
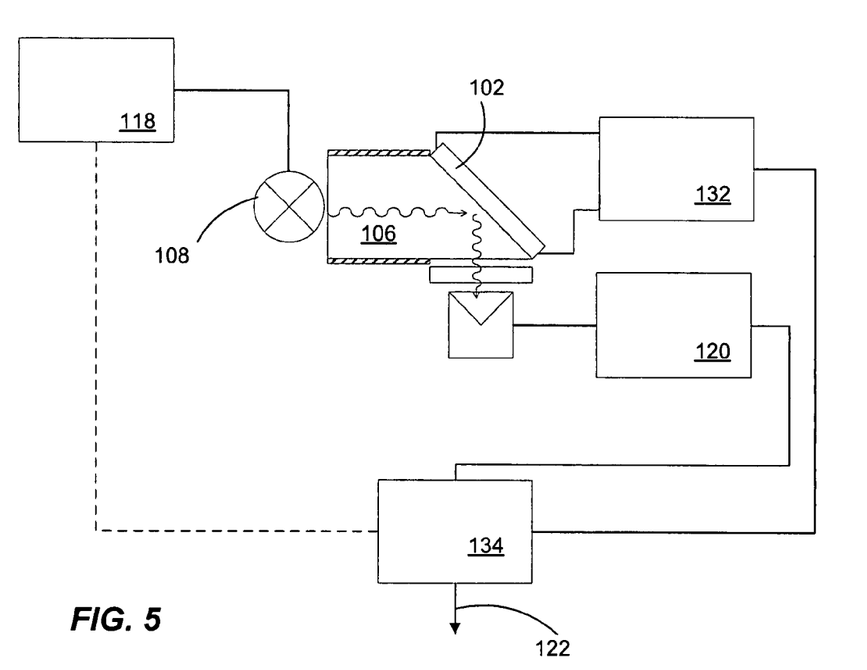
FIG. 5 is a schematic view of a hydrogen sensor with redundant analysis using two hydrogen-dependent sensor principles.

In the case of a gas sensor arrangement 100 for hydrogen in particular, which is based on hydrogen-sensitive metallization layers, the reflectivity of which is modified by inclusion of the analyte, there is also the particularly elegant possibility of providing a redundancy branch 124 as shown in FIG. 5. The arrangement shown here is based on the fact that, in the case of a nickel-magnesium layer in accordance with B. Farangis et al "A ROOM-TEMPERATURE OPERATED HYDROGEN SENSOR BASED ON NICKEL-MAGNESIUM FILMS", Poc. Of the 20th EUROSENSORS, Göteborg, Sweden, 17th-19th Sep. 2006, Paper T1C-P5, not only the optical characteristics but also electrical conductivity are modified by inclusion of hydrogen.

According to the invention, the measuring transducer can, in addition to optical evaluation by detector 112, be in electrical contact and its impedance can be measured by another evaluation circuit 132. A central control unit 134 receives the signals from the evaluation circuits 120 and 132 and determines an output value 122 after plausibility checks. There can also be provision for the central control unit 134 to correct the control circuit of the radiation source 118 accordingly. The basic idea behind this variant which is shown in FIG. 5 is the fact that it is possible to draw conclusions regarding the ageing of the radiation source 108 by analyzing an effect which is independent of the radiation source and its condition. Such diversified analysis can fulfill a safety function in an especially simple manner. In the simplest case, the transducer layer 102 is structured with defined dimensions so that it is possible to measure its ohmic resistance as a redundancy branch.

Another advantageous embodiment of the present invention is explained in more detail below, reference being made to FIG. 6. This embodiment is based on the concept of using an entire additional gas sensor arrangement, in this case a $CO_2$ sensor which operates on the Non-Dispersive Infra-Red (NDIR) principle and uses the same radiation source 108 as the hydrogen sensor components, as the redundancy branch 124.

Such a combined gas sensor arrangement makes it possible, for instance, to detect hydrogen as well as carbon dioxide (or another polar gas) using a single component and, besides ensuring redundancy and a concomitant improvement in operational reliability, also has the advantage that the radiation source 108 can be used centrally—this has a cost benefit and also improves safety-relevant plausibility checks.

The absorption measuring path 136 of the NDIR sensor can then be designed as a measuring cuvette which is integral with the transparent light conducting body 106 for the $H_2$ sensor in the form of a common injection-molded part made of plastic material. The hydrogen-sensitive layer can then be applied in the location provided by using an inexpensive batch process.

The combined gas sensor arrangement according to the invention which has an absorption measuring path for detecting a polar gas as well as a hydrogen-sensitive layer which modifies reflection and a light conducting body in accordance with the present invention, can be fabricated as an integrated unit which allows the use of Surface Mount Technology (SMT). This will be explained in more detail later, making reference to FIG. 11.

Figure 6:
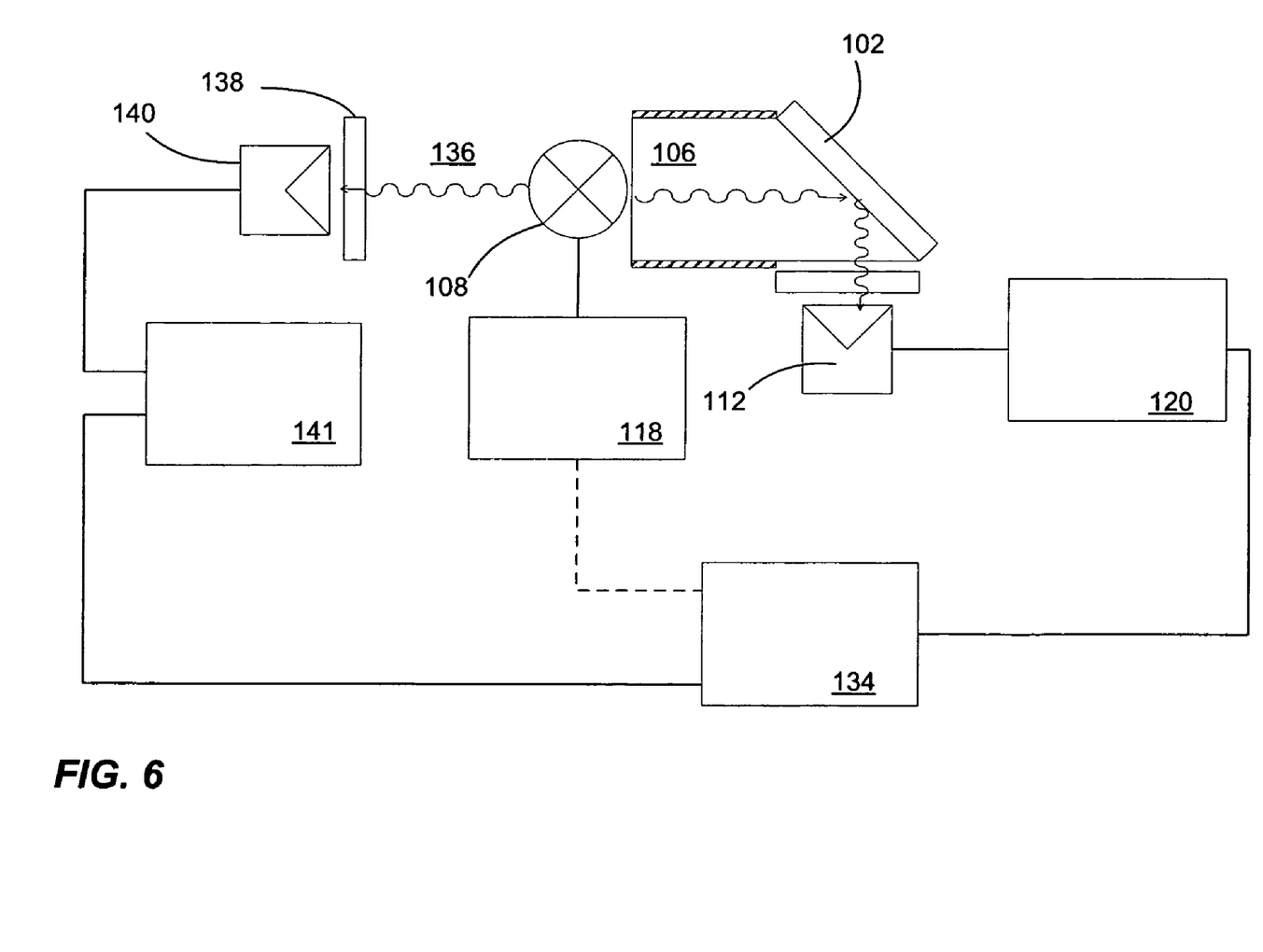
FIG. 6 is a combination of an infrared gas sensor and a hydrogen sensor in accordance with a first embodiment.

The combined gas sensor arrangement according to FIG. 6 can be equipped with some or all of the redundancy branches shown in the previous embodiments.

Figure 7:
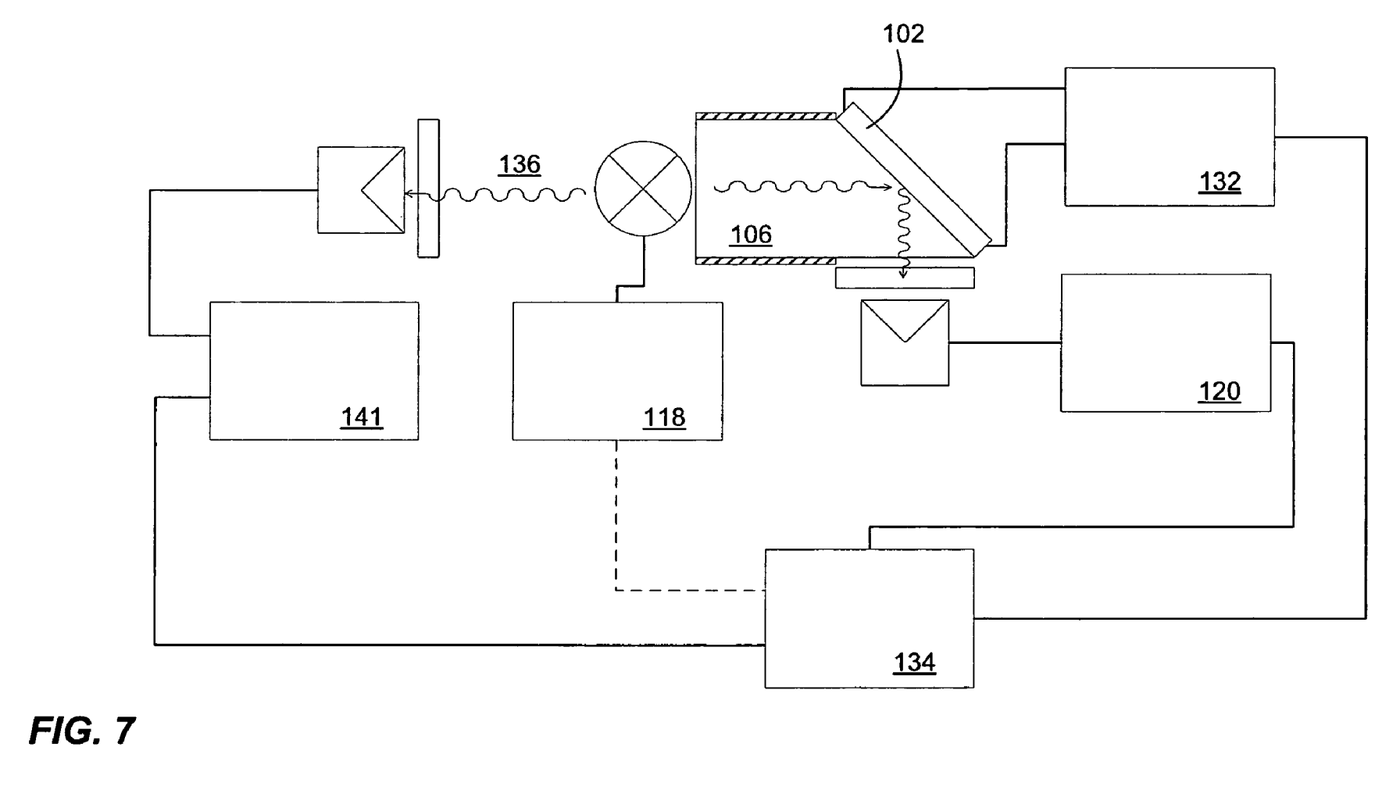
FIG. 7 is a schematic view of a combined gas sensor arrangement based on the embodiments in FIGS. 5 and 6.

FIG. 7, for example, shows a case in which the electrical resistance can also be sensed on the hydrogen-sensitive layer 102 in order to compensate the state of ageing of radiation source 108.

Figure 8:
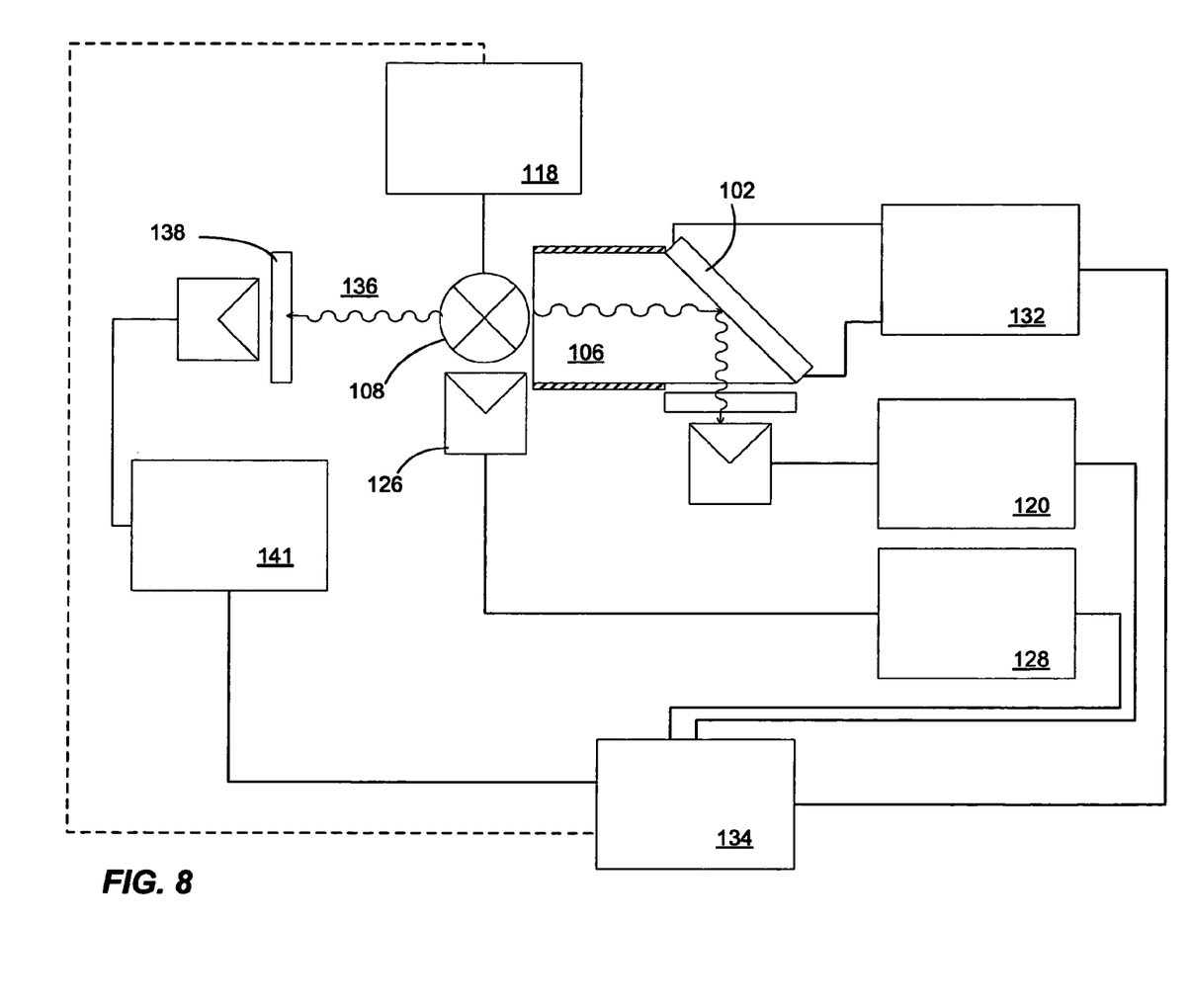
FIG. 8 is a schematic view of a combined gas sensor arrangement with an additional detector for monitoring lamp ageing.

FIG. 8 shows an embodiment in which another detector element 126, 136, 138 is used in order to directly monitor the characteristics of the radiation source 108 and exclude the effects of the absorption measuring path 136, the light conducting body 106 and the measuring transducer layer 102. Although the evaluation circuits and control units shown here are depicted as separate units, it is clear to a person skilled in the art that all these control functions can be implemented in a single component.

The NDIR gas sensor component for detecting a polar gas also comprises, according to another advantageous embodiment and as is conventional with such familiar arrangements, a transmission filter 138 which only allows the wavelength of interest to reach the detector unit 140, for example 4.25 μm in the case of $CO_2$. As with the embodiments shown above, the central control unit 134 receives signals from the evaluation circuit 141 coupled to the detector unit 140 similarly to evaluation circuit 120, discussed above, to determine an output value 122 after plausibility checks.

Combining a hydrogen sensor with an NDIR sensor for polar gases in accordance with the invention makes it possible, in the context of automotive applications in particular, to achieve especially compact, affordable construction and also makes it possible to compensate ageing of the optical radiation source and perform plausibility checks on the entire sensor system. The diversified analysis performed by the hydrogen-selective coating makes it possible to achieve long-term stability, accuracy and reliability and the shared use of one optical radiation source as opposed to two separate individual sensors for hydrogen and for carbon dioxide provides a significant advantage in terms of space and cost savings.

Figure 9:
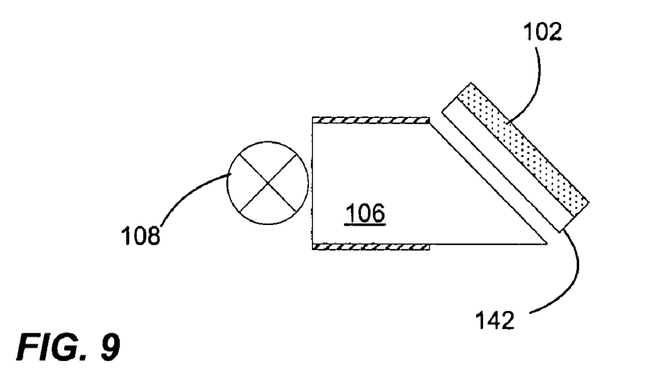
FIG. 9 is a first implementation of a hydrogen sensor light-conducting-body with a metallic measuring transducer layer on a separate support.
Figure 10:
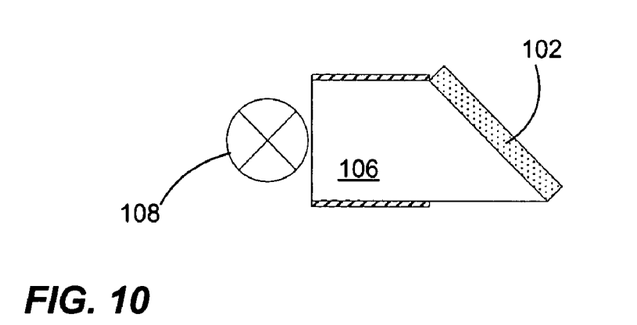
FIG. 10 is a second embodiment of a light conducting body with a directly deposited hydrogen-sensitive layer.

Various possible ways of producing a hydrogen-sensitive measuring transducer are compared with each other in FIGS. 9 and 10. As shown in FIG. 9, the transducer layer 102 can be applied on an individual support 142 and be provided with appropriate electrical connections if necessary. The support 142 is then mounted on the light conducting body 106. This embodiment has the advantage that planer supports 142 such as this are easier to coat than three-dimensional light conducting bodies. However, exacting requirements are placed on the boundary areas of the light conducting body 106 and the support plate 142 which come into contact with each other and through which the measurement radiation 110 impinges on the sensitive layer 102. This is why, under certain conditions, the embodiment shown in FIG. 10 where the hydrogen-sensitive measuring transducer layer 102 is applied directly onto the light conducting body 106, using sputtering technology for example, may be preferable.

Figure 11:
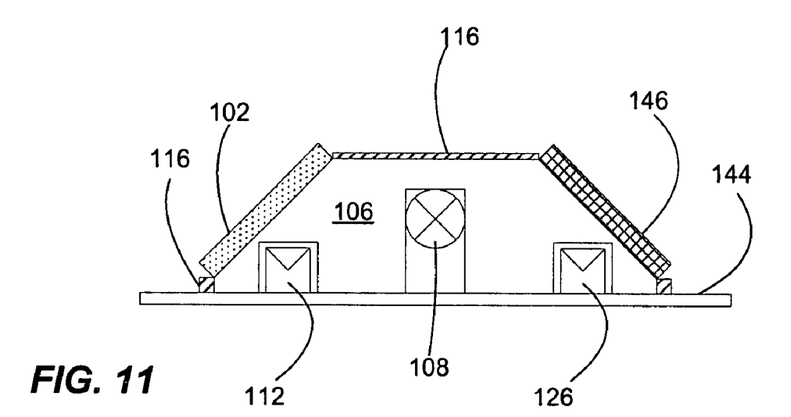
FIG. 11 is a schematic cross-section through an integrated hydrogen sensor arrangement mounted on a circuit carrier.

A surface mountable configuration of the hydrogen sensor according to the invention which is essentially in accordance with the redundancy principle in FIG. 3 is shown schematically in FIG. 11. A circuit carrier 144, for instance a printed circuit board (PCB) accommodates a radiation source 108 as well as two detectors 112, 126. The light conducting body 106 is mounted above these elements and the light conducting body has a hydrogen-selective transducer layer 102, which is in contact with a measured medium 104, on the same side as the actual measuring detector 112. The inactive surface of the light conducting body 106 is covered with an optically opaque layer 116. In order to be able to assess possible interference due to the radiation source 108 or temperature in isolation from hydrogen-selective affects, a simple non-selective mirror layer 146 is applied on the same side as the redundant detector 126 symmetrically with respect to the transducer layer 102. The evaluation circuits, which are not shown here, can be arranged on the same circuit carrier 144 or be provided separately from the gas sensor arrangement in FIG. 11. A cuvette for detecting $CO_2$ can be added in the same plane of projection.

One significant advantage of the arrangement shown in FIG. 11 is the fact that the light conducting body 106 can be replaced easily without having to replace the expensive components that are permanently attached to the circuit board 144 if the light conducting body is contaminated through contact with the measured medium 104 or if appropriate guidelines demand such replacement. The light conducting body 106 as such is a disposable part which can be cheaply mass-produced. This means that using such an arrangement in future vehicles that are powered by hydrogen or which use a fuel cell makes very good sense.

The foregoing illustrates some of the possibilities for practicing the invention. Many other embodiments are possible within the scope and spirit of the invention. It is, therefore, intended that the foregoing description be regarded as illustrative rather than limiting, and that the scope of the invention is given by the appended claims together with their full range of equivalents.

What is claimed is:

1. An optical sensor arrangement for detecting at least one analyte in a measured medium comprising:
   at least one radiation source for emitting radiation,
   at least one measuring transducer wherein optical characteristics and a physical characteristic of the measuring transducer are modified in response to the presence and/or concentration of the analyte in the measured medium and the measuring transducer is arranged so that the measuring transducer interacts with at least part of the emitted radiation,
   a first detector unit for capturing a change in radiant intensity as a result of the modified optical characteristics of the measuring transducer and for outputting a first measuring signal,
   at least a second detector unit set up in order to capture the change in the physical characteristic,
   a light conducting body which is transparent to the emitted radiation with the measuring transducer, which is sensitive to the analyte, being arranged on at least one surface of the light conducting body so that the emitted radiation impinges on a surface of the measuring transducer which faces away from the measured medium, wherein the measuring transducer is sloped relative to the direction of emitted radiation so that at maximum reflectivity, approximately all the radiation is reflected towards the first detector unit, and
   at least a second measuring transducer which comprises an absorption measuring path being integral with the light conducting body for detecting a polar gas, wherein the radiation source is positioned centrally with respect to the measuring transducer and the second measuring transducer.

2. A sensor arrangement according to claim 1, wherein first measuring transducer comprises a hydrogen-sensitive metallic mirror layer, the reflectivity of which changes in response to the presence and/or concentration of hydrogen.

3. A sensor arrangement according to claim 2, wherein the first measuring transducer comprises a magnesium-nickel alloy layer.

4. A sensor arrangement according to claim 2, wherein the first measuring transducer has a palladium covering layer.

5. A sensor arrangement according to claim 4, wherein the radiation is infrared radiation and the at least one radiation source consists of an infrared radiation source, which emits a broadband light spectrum, or a light-emitting diode.

6. A sensor arrangement according claim 5, wherein the second detector unit generates a correction signal in order to calibrate at least the first measuring signal.

7. A sensor arrangement according to claim 6, wherein the other physical characteristic is an electrical impedance and the second detector unit comprises an impedance-measuring device.

8. A sensor arrangement according to claim 7, wherein the second detector unit has an optical detector unit which directly captures the radiant intensity of the radiation source.

9. A sensor arrangement according to claim 1, wherein a cuvette which constitutes the absorption measuring path as the second measuring transducer is formed in the light-conducting body.

10. A sensor arrangement according to claim 9 which has at least one other detector unit for detecting a change in radiant intensity due to the changed optical characteristics of the second measuring transducer and for outputting a second measuring signal.

11. A sensor arrangement according to claim 10, wherein the second measuring transducer is for detecting carbon dioxide.

12. A sensor arrangement according to claim 11 further comprising a reference radiation source for monitoring the state of ageing of the radiation source.

13. A sensor arrangement according to claim 12, wherein at least the radiation source, the light conducting body and the detector unit are mounted on a circuit carrier.

14. A sensor arrangement according to claim 13, wherein the light conducting body is made of plastic material by injection molding.

15. A sensor arrangement according to claim 14, wherein the first measuring transducer is deposited on the light conducting body as a metallic mirror layer by sputtering or evaporation.

16. A sensor arrangement according to claim 1, wherein the second measuring transducer is a non-dispersive infrared (NDIR) sensor.

17. An optical sensor arrangement for detecting at least one analyte in a measured medium comprising:
- a radiation source,
- a reference radiation source being operated intermittently to approximately retain its initial operating condition,
- at least one measuring transducer wherein optical characteristics and a physical characteristic of the measuring transducer are modified in response to the presence and/or concentration of the analyte in the measured medium and the measuring transducer is arranged so that the measuring transducer interacts with at least part of the emitted radiation,
- a first detector unit for capturing a change in radiant intensity as a result of the modified optical characteristics of the measuring transducer and for outputting a first measuring signal,
- an evaluation circuit which compares the measuring signal generated from the radiation source to the measuring signal generated from the reference radiation source intermittently to generate a compensation related to the aging of the radiation source as compared to the reference radiation source, and
- a light conducting body which is transparent to the emitted radiation with the measuring transducer, which is sensitive to the analyte, being arranged on at least one surface of the light conducting body so that the emitted radiation impinges on a surface of the measuring transducer which faces away from the measured medium, wherein the measuring transducer is sloped relative to the direction of emitted radiation so that at maximum reflectivity, approximately all the radiation is reflected towards the first detector unit, and
- at least a second measuring transducer which comprises an absorption measuring path being integral with the light conducting body for detecting a polar gas, wherein the radiation source is positioned centrally with respect to the measuring transducer and the second measuring transducer.

18. A sensor arrangement according to claim 17 further comprising at least a second detector unit set up in order to capture the change in the physical characteristic.

19. A sensor arrangement according to claim 17, wherein the second measuring transducer is a non-dispersive infrared (NDIR) sensor.

20. An optical sensor arrangement for detecting at least one analyte in a measured medium comprising:
- at least one radiation source for emitting radiation,
- at least one measuring transducer wherein optical characteristics and a physical characteristic of the measuring transducer are modified in response to the presence and/or concentration of the analyte in the measured medium and the measuring transducer is arranged so that the measuring transducer interacts with at least part of the emitted radiation,
- a first detector unit for capturing a change in radiant intensity as a result of the modified optical characteristics of the measuring transducer and for outputting a first measuring signal,
- at least a second detector unit arranged on a redundancy branch so that it interacts with at least a different part of the emitted radiation for outputting a second measuring signal, and
- a light conducting body which is transparent to the emitted radiation with the measuring transducer, which is sensitive to the analyte, being arranged on at least one surface of the light conducting body so that the emitted radiation impinges on a surface of the measuring transducer which faces away from the measured medium, wherein the measuring transducer is sloped relative to the direction of emitted radiation so that at maximum reflectivity, approximately all the radiation is reflected towards the first detector unit, and
- at least a second measuring transducer which comprises an absorption measuring path being integral with the light conducting body for detecting a polar gas, wherein the radiation source is positioned centrally with respect to the measuring transducer and the second measuring transducer.

21. A sensor arrangement according to claim 20 further comprising a central control unit which receives the first and second measuring signals and corrects a control circuit which controls the radiation source.

22. A sensor arrangement according to claim 20, wherein the second measuring transducer is a non-dispersive infrared (NDIR) sensor.

* * * * *